United States Patent [19]

Rose et al.

[11] 4,314,809

[45] Feb. 9, 1982

[54] NOVEL COUPLER COMPONENTS FOR OXIDATION HAIR DYES, THE MANUFACTURE THEREOF, AND HAIR COLORANTS

[75] Inventors: David Rose, Hilden; Peter Busch, Erkrath-Unterbach; Edgar Lieske, Düsseldorf; Günther Konrad, Hilden, all of Fed. Rep. of Germany

[73] Assignee: Henkel Kommanditgesellschaft auf Aktien, Düsseldorf-Holthausen, Fed. Rep. of Germany

[21] Appl. No.: 94,276

[22] Filed: Nov. 14, 1979

[30] Foreign Application Priority Data

Dec. 2, 1978 [DE] Fed. Rep. of Germany ....... 2852156
Aug. 10, 1979 [DE] Fed. Rep. of Germany ....... 2932460

[51] Int. Cl.$^3$ .......................... A61K 7/13; D06P 1/32; D06P 3/08
[52] U.S. Cl. ........................................... 8/406; 8/421; 8/424; 564/305; 564/428; 564/443
[58] Field of Search ........................... 8/406, 421, 424; 564/428, 443, 305

[56] References Cited

U.S. PATENT DOCUMENTS

| | | | |
|---|---|---|---|
| 1,210,751 | 1/1917 | Anderwert et al. | 564/305 X |
| 2,204,230 | 6/1940 | Rossander et al. | 564/305 X |
| 3,452,038 | 6/1969 | Randall et al. | 564/305 X |
| 3,654,364 | 4/1972 | Meckel et al. | 564/305 |
| 3,862,226 | 1/1975 | Harfenist | 564/305 X |
| 4,161,474 | 7/1979 | Campbell et al. | 564/305 X |

FOREIGN PATENT DOCUMENTS 1556140 11/1979 United Kingdom ................ 564/305

OTHER PUBLICATIONS

Ashley et al., "J. Chem. Soc.", pp. 3298–3313 (1958).

*Primary Examiner*—John Doll
*Attorney, Agent, or Firm*—Hammond & Littell, Weissenberger and Muserlian

[57] ABSTRACT

This invention is directed to novel bis-(2,4-diaminophenoxy)-alkanes and a method of preparing them. This invention is also directed to the use of said bis-(2-4-diaminophenoxy)-alkanes, or the salts thereof, as coupler components in developer-coupler oxidation hair dyeing compositions.

6 Claims, No Drawings

NOVEL COUPLER COMPONENTS FOR OXIDATION HAIR DYES, THE MANUFACTURE THEREOF, AND HAIR COLORANTS

FIELD OF THE INVENTION

This invention is directed to novel coupler components. More specifically, this invention is directed to novel coupler components for oxidation hair dyes, the manufacture thereof, and hair colorants containing such hair dyes.

BACKGROUND OF THE INVENTION

The subject matter of the invention are new bis-(2,4-diaminophenoxy)-alkanes of the general formula

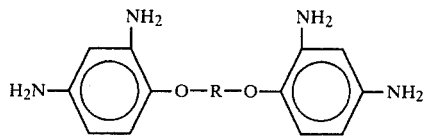

wherein R represents a linear or branched alkylene radical with from about 1 to 12 carbon atoms.

The production of the bis-(2,4-diaminophenoxy)-alkanes of Formula I is generally a four-stage process which comprises the following stages:

1st stage:
Acetylation of 2-amino-4-nitrophenol to 2-acetylamino-4-nitrophenol;

2nd stage:
Reaction of 2-acetylamino-4-nitrolphenol with dibromoalkane to form bis-(2-acetylamino-4-nitrophenoxy)-alkanes;

3rd stage:
Splitting off the acetyl groups of the bis-(2-acetylamino-4-nitrophenoxy)-alkanes by boiling with hydrochloric acid to form bis-(2-amino-4-nitrophenoxy)-alkanes; and 4th stage:
Catalytic reduction of the bis-(2-amino-4-nitrophenoxy)-alkanes to form bis-(2,4-diaminophenoxy)-alkanes.

The reactions of the first three stages are described more fully in German Published Application (DOS) No. 26 58 329, while the reaction according to the fourth stage is based on hydrogenation methods known from the literature. Such a four-stage production process is very elaborate, and thus there has been a need for a simpler method.

OBJECTS OF THE INVENTION

It is an object of this invention to provide a novel coupler component for hair dyes.

It is also an object of this invention to provide a process for manufacturing the coupler component.

It is further an object of this invention to provide hair colorants based on said hair dyes.

These and other objects of the invention will become more apparent in the discussion below.

DETAILED DESCRIPTION OF THE INVENTION

It has been surprisingly found that the compounds of Formula I can be prepared via a better, less complex process. The process comprises the steps of:

(a) reacting 2,4-dinitrophenol with a base to form 2,4-dinitrophenolate-anion;

(b) reacting the 2,4-dinitrophenolate-anion with a dibromoalkane of formula Br-R-Br wherein R is as defined above, to form bis-(2,4-dinitrophenoxy)-alkane;

(c) separating 2,4-dinitrophenol from the bis-(2,4-dinitrophenoxy)-alkane by washing with a base; and (d) converting the bis-(2,4-dinitrophenoxy)-alkane in known manner by catalytic hydrogenation to the corresponding bis-(2,4-diaminophenoxy)-alkane.

Suitable bases for converting 2,4-dinitrophenol to 2,4-dinitrophenolate-anion include potassium carbonate, potassium hydroxide, and the like. Solvents useful for carrying out the reaction of step (a) or (b) include dimethyl formamide, methyl-glycol, diethylene glycol monomethyl ether and diethylene glycol dimethyl ether. Preferably the same solvent is employed in each step, and the reaction mixture from step (a) is then reacted in step (b) without separation of the 2,4-dinitrophenolate-anion.

The reaction of step (a) is carried out at temperatures of from about 80° to 200° C., preferably of from about 100° to 150° C. The reaction of step (b) is carried out at temperatures of from 80° to 200° C., preferably from about 100° to 150° C., for from about 0.5 to 12 hours.

The base used in step (c) can be any of the bases typically employed for such a purpose. Suitable bases include solutions of, for example, soda lye, i.e., sodium hydroxide, potassium hydroxide, and the like.

There are many catalysts known to those skilled in the art that would be useful in the catalytic hydrogenation of step (d); however, Raney nickel or palladium on carbon are preferred.

In a preferred embodiment of the invention, the compounds of Formula I are prepared by the steps of:

(a) reacting 2,4-dinitrophenol with potassium carbonate or potassium hydroxide in a suitable solvent at a temperature of from about 100° to 150° C.;

(b) reacting the reaction mixture from step (a) with a dibromoalkane of formula Br-R-Br wherein R is as defined above at a temperature of from about 100° to 150° C. for from about 0.5 to 12 hours to form bis-(2,4-dinitrophenoxy)-alkane;

(c) separating 2,4-dinitrophenol from the bis-(2,4-dinitrophenoxy)-alkane by washing with a base; and (d) converting the bis-(2,4-dinitrophenoxy)-alkane by catalytic hydrogenation wherein Raney nickel or palladium on carbon is employed as catalyst, to the corresponding bis-(2,4-diaminophenoxy)-alkane.

The process according to the invention permits a simple, less complex, commercial production of the abovedescribed bis-(1,3-diaminophenoxy)-alkanes.

Other aspects of the invention concern the use of the bis-(2,4-diaminophenoxy)-alkanes as such, or in the form of their salts, with inorganic or organic acids as coupler components in oxidation hair dyes, and hair dyes containing the bis-(2,4-diaminophenoxy)-alkanes or their salts.

The so-called oxidation dyes, which are formed by oxidative coupling of a developer component with a coupler component, play an important role in the dyeing of hair because of their intensive colors and very good fastness properties. Nitrogen bases, such as p-phenylene diamine derivatives, diaminopyridines, 4-aminopyrazolone derivatives, heterocyclic hydrazones, and the like, are normally used as developer compounds. The so-called oxidation dyes, which are formed by oxidative coupling of a developer component with a coupler component, play an important role in the dyeing of hair because of their intensive colors and very good fastness properties. Nitrogen bases, such as p-phenylene diamine derivatives, diaminopyridines, 4-aminopyrazolone derivatives, heterocyclic hydrazones, and the like, are normally used as developer compounds. The so-called coupler components include m-phenylene-diamine derivatives, phenols, naphthols, resorcinol derivatives, pyrazolones, and the like.

Good oxidation hair dye components must meet primarily the following conditions:

In oxidative coupling with the respective developer or coupler components, they must form the desired color shades with sufficient intensity. They must also have good to excellent absorption power on human hair, and they should also be harmless in toxicological and dermatological respects.

In the search for suitable oxidation hair dyes, the problem has therefore been to find suitable components which meet the above-mentioned conditions in an optimum manner.

It has been found that it is possible to obtain oxidation hair dyes which meet the above-mentioned conditions to a very high degree by using as coupler components bis-(2,4-diaminophenoxy)-alkanes of the general Formula I, wherein R denotes a linear or branched alkylene radical with from about 1 to 12 carbon atoms, as well as their inorganic or organic salts, in combination with conventional developer substances.

Hair colorants based on oxidation hair dyes with a content of bis-(2,4-diaminophenoxy)-alkanes of the general Formula I, where R denotes a linear or branched alkylene radical with from about 1 to 12 carbon atoms, or their inorganic or organic salts, as coupler components and the developer substances normally used in oxidation hair dyes, thus represent especially valuable compositions in the oxidation hair dye field.

Of particular importance are the coupler components wherein in Formula I, R denotes a linear alkylene radical with from 1 to 4 carbon atoms.

When the compounds according to the invention are used as coupler components with the developer substances generally used in oxidation hair dyeing, the resulting hair dye compositions produce highly intensive shades from turquoise to blue-black and therefore enrich the hair-dyeing possibilities quite considerably. Beyond that, the bis-(2,4-diaminophenoxy)-alkanes are characterized by excellent fastness of the resulting color tones, by good solubility in water, by good stability in storage, and by toxicological and dermatological acceptability.

The bis-(2,4-diaminophenoxy)-alkanes to be used as coupler components according to the invention can be used either as such or in the form of their salts with inorganic or organic acids, such as chlorides, sulfates, phosphates, acetates, propionates, lactates, ditrates, and the like.

Compounds according to the invention useful as coupler components include, for example, bis-(2,4-diaminophenoxy)-methane, 1,2-bis-(2,4-diaminophenoxy)-ethane, 1,3-bis-(2,4-diaminophenoxy)-propane, 1,4-bis-(2,4-diaminophenoxy)-butane, 1,5-bis-(2,4-diaminophenoxy)-pentane, 1,6-bis-(2,4-diaminophenoxy)-hexane, 1,8-bis-(2,4-diaminophenoxy)-octane, 1,10-bis-(2,4-diaminophenoxy)-decane, 1,12-bis-(2,4-diaminophenoxy)-dodecane, 1,2-bis-(2,4-diaminophenoxy)-propane, 1,3-bis-(2,4-diaminophenoxy)-2-methyl propane, and 1,6-bis-(2,4-diaminophenoxy)-2-methylhexane.

Many of the developer substances used in hair dyes and known in the art can be employed with the compounds of Formula I. More particularly, useful developers include primary aromatic amines with an additional functional group in the p-position, such as p-phenylene diamine, p-tolylene diamine, p-aminophenol, N-methyl-p-phenylene-diamine, N,N-dimethyl-p-phenylene diamine, N,N-diethyl-2-methyl-p-phenylene diamine, N-ethyl-N-hydroxyethyl-p-phenylene diamine, chlorine-p-phenylene diamine, N,N-bis-hydroxyethylamino-p-phenylene diamine, methoxy-p-phenylene diamine, 2,6-dichloro-p-phenylene diamine, 2-chloro-6-bromo-p-phenylene diamine, 2-chloro-6-methyl-p-phenylene diamine, and 6-methoxy-3-methyl-p-phenylene diamine, and other compounds of the above-mentioned type, which have one or more additional additional groups, such as hydroxyl or amino groups, or NHR' or NR'$_2$ wherein R' denotes an alkyl or hydroxyalkyl radical with from 1 to 4 carbon atoms. Also useful in this respect are diamino pyridine derivatives, heterocyclic hydrazone derivatives, such as 1-methyl-pyrrolidone-(2)-hydrazone, 4-amino-pyrazoline derivatives, such as 4-amino-1-phenyl-3-carbamoyl pyrazolone-5, N-butyl-N-sulfobutyl-p-phenylene diamine, tetraaminopyrimidines, such as 2,4,5,6-tetraaminopyrimidine, 4,5-diamino-2,6-bismethylaminopyrimidine, 2,5-diamino-4-diethylamino-6-methylaminopyrimidine, 2,4,5-triamino-6-dimethylaminopyrimidine, 2,4,5-triamino-6-piperidino-pyrimidine, 2,4,5-triamino-6-anilino-pyrimidine, 2,4,5-triamino-6-morpholino-pyrimidine, and 2,4,5-triamino-6-($\beta$-hydroxyethyl)aminopyrimidine.

To obtain strong color tones corresponding as much as possible to the natural hair shades, it is necessary to use a superior blue dye as a shading component. There are frequently difficulties with the conventional blue couplers in obtaining natural blue shades by means of blue coupler components. This can be avoided to a great extent by using the bis-(2,4-diaminophenoxy)-alkanes according to the invention. In use with corresponding developer substances these coupler components yield, in addition to other shades, dark-blue to black-blue, particularly intensive hair colorations which are characterized by excellent fastness to light.

In the hair dyes according to the invention, the coupler components are generally used in substantially molar quantities, based on the developer substances used. Though the molar application, i.e., a molar ratio of 1:1, is preferable, the coupler component can also be used in excess or in less than the molar amount. In practice, the molar ratio of coupler to developer can range from about 0.5:1 to about 2:1.

In addition, it is not necessary that the developer component and the coupler substance represent homogeneous products. Rather, the developer components can be mixtures of the developer compounds to be used and the coupler substance can be a mixture of the bis-(2,4-diaminophenoxy)-alkanes to be used according to the invention.

Beyond that, the hair dyes according to the invention can contain conventional, directly absorbing dyes in mixture, if such is necessary to obtain certain shades.

The oxidative coupling, that is, the development of the coloration, can be effected principally by atmospheric oxygen, as in other oxidation hair dyes. Preferably, however, chemical oxidants are used. Useful chemical oxidants include, in particular, hydrogen peroxide or its addition products on urea, melamine and sodium borate, as well as mixtures of these hydrogen peroxide addition compounds with potassium peroxide disulfate.

The bis-(2,4-diaminophenoxy)-alkanes to be used according to the invention have the additional advantage that they already yield satisfactory results in oxidative coupling with atmospheric oxygen. Thus, damage to the hair by oxidants otherwise used for the oxidative coupling can be avoided. However, if a brightening effect is to be achieved in addition to the coloring, the use of oxidants is absolutely necessary.

The hair dyes according to the invention can be incorporated into corresponding cosmetic preparation, such as creams, emulsions, gels, or simple solutions, and are mixed with one of the above-mentioned oxidants directly before they are applied to the hair. The concentrations of the coupler-developer combination in these dyes is from about 0.2 to 5% by weight, preferably from about 1 to 3% by weight. For the preparations of creams, emulsions, or gels, by dye components are mixed with the other components used in these preparations. Such additional components include, for example, wetting agents or emulsifiers of the anionic or nonionogenic type, such as alkyl benzene sulfonates, fatty alcohol sulfates, alkyl sulfonates, fatty acid alkanol amides, and addition products of ethylene oxide on fatty alcohols; thickeners, such as methyl cellulose, starch, higher fatty alcohols, paraffin oil, and fatty acids; and also perfume oils and hair preparations such as pantothenic acid and cholesterol. The above-mentioned additives are used in the amounts customary for these purposes, such as wetting agents and emulsifiers in concentrations of from about 0.5 to 30% by weight, and thickeners in concentrations of from about 0.1 to 25% by weight, each based on the weight of the total preparation.

Regardless of whether a cream, a solution, an emulsion, or a gel is used, the hair dyes according to the invention can be applied in a weakly acid medium, a neutral medium, or, particularly, an alkaline medium with a pH of from 8 to 10. The application temperatures range from about 15° to 40° C. After about 30 minutes, the dye is removed by rinsing from the hair to be dyed. Then the hair is washed with a mild shampoo and dried.

The blue tints obtained with the dyes according to the invention show particularly intensive shades with the use of different developer and coupler components. The colors are fast to light, washing, and rubbing, and can be easily removed with reducing agents.

The following Examples are intended to illustrate the subject of the invention and are not to be construed as limiting the invention thereto.

EXAMPLES

The preparation of bis-(2,4-diaminophenoxy)-alkanes, both according to a conventional method and according to the improved method of the invention are described:

Comparative Examples A to D

The bis-(2-amino-4-nitrophenoxy)-alkanes serving as intermediate products according to the conventional method were obtained according to German Published Application (DOS) No. 2 658 329, incorporated herein by reference, by reacting 2 mols of the correspondingly substituted 2-acetylamino-4-nitrophenol with somewhat more than 1 mol of corresponding dibromoalkane in the presence of somewhat more than 2 mols of alkali-hydroxide in an aqueous-alcoholic medium at temperatures of from about 100° and 150° C. to form the bis-(2-acetylamino-4-nitrophenoxy)-alkane compounds, and then removing the acetyl radicals by boiling with hydrochloric acid.

The following compounds were prepared:

(A)

Bis-(2,4-diaminophenoxy)-methane-tetrahydrochloride

An amount of 10.4 g bis-(2-amino-4-nitrophenoxy)-methane, prepared as described above, using dibromomethane was hydrogenated in 200 ml of ethanol and 20 ml of dimethyl formamide in the presence of 1.0 g of Raney nickel at 80° C. and 100 atm. (gauge). After the hydrogen absorption was complete, the substance was filtered off from the catalyst and concentrated until dry. The residue was dissolved in dilute hydrochloric acid, and the resulting solution was dissolved in dilute hydrochloric acid. That solution was concentrated to dryness. The residue was dried at 70° C., and 7.8 g of bis-(2,4-diaminophenoxy)-methane-tetrahydrochloride were obtained. The compound melted at 210° C. under decomposition.

(B)

1,2-Bis-(2,4-diaminophenoxy)ethane-tetrahydrochloride

In accordance with the procedure in (A), 11.5 g of 1,2-bis-(2-amino-4-nitrophenoxy)-ethane were hydrogenated in 300 ml of ethanol and 150 ml of water in the presence of 1.0 g of a hydration catalyst (5% palladium on carbon) and worked up. The yield of 1,2-bis-(2,4-diaminophenoxy)-ethane-tetrahydrochloride with a melting point of 179°–181° C. was 12.0 g.

(C)

1,3-Bis-(2,4-diaminophenoxy)-propane-tetrahydrochloride

In accordance with the procedures of (A), 10.6 g of 1,3-bis-(2-amino-4-nitrophenoxy)-propane were hydrogenated in 150 ml of dimethyl formamide in the presence of 1.0 g of Raney nickel and worked up. The yield of 1,3-bis-(2,4-diaminophenoxy)-propane-tetrahydrochloride was 9.1 g. The compound melted at 165° C. under decomposition.

(D)

1,4-Bis-(2,4-diaminophenoxy)-butane-tetrahydrochloride

Following the procedure of (A), 8.8 g of 1,4-bis-(2-amino-4-nitrophenoxy)-butane were hydrogenated in 150 ml of dimethyl formamide in the presence of 1.0 g of Raney nickel and worked up. The yield of 1,4-bis-(2,4-diaminophenoxy)-butane-tetrahydrochloride was 8.2 g. The compound melted at 222° to 240° C. under decomposition.

The method of this invention was employed to prepare 1,3-bis-(2,4-diaminophenoxy)-propane-tetrahydrochloride as follows:

EXAMPLE 1

Stage 1: Preparation of 1,3-bis-(2,4-dinitrophenoxy)-propane

An amount of 9.2 g of 2,4-diaminophenol, moistened with 0.6 g of water, was suspended in 15 ml of dimethylene glycol dimethyl ether. To the suspension were added 3.45 g of potassium carbonate at about 25° C. The suspension was then heated to 100° C., and 5 g of 1,3-dibromopropane were added in drops. Subsequently the suspension was heated for four hours to 125° C. After cooling, the precipitate was separated and washed first with soda lye and then with water. After drying, the 1,3-bis-(2,4-dinitrophenoxy)-propane obtained had a melting point of 186° C. The yield was 8.2 g, that is, 80% of theory.

Stage 2: Preparation of 1,3-bis-(2,4-diaminophenoxy)-propane-tetrahydrochloride

Ten grams of 1,3-bis-(2,4-dinitrophenoxy)-propane were hydrogenated in 50 ml of ethanol in the presence of Raney nickel at 25 atm. (gauge) and 25° C. After the hydrogen absorption was complete, the product was distilled off from the catalyst. The solution was acidified with concentrated hydrochloric acid and concentrated to dryness. The 1,3-bis-(2,4-diaminophenoxy)-propane-tetrahydrochloride was obtained in the form of white crystals with a melting point of 215° C. in a yield of 96% of theory.

EXAMPLE 2

Stage 1

The preparation of 1,3-bis-(2,4-dinitrophenoxy)-propane was similar to that in Example 1, with the exception that 2.8g of potassium hydroxide, rather than potassium carbonate, were added to the suspension of 2,4-dinitrophenol in diethyleneglycol dimethylether. The yield of 1,3-bis-(2,4-dinitrophenoxy)-propane was 6.6 g, that is, 64% of theory.

Stage 2

Corresponded completely to Stage 2 of Example 1.

EXAMPLE 3

Stage 1

The preparation of 1,3-bis-(2,4-dinitrophenoxy)-propane was similar to that of Example 1, with the exception that 15 ml of methyl glycol were used as a solvent. The yield of 1,3-bis-(2,4-dinitrophenoxy)-propane was 6.6 g, that is, 64% of theory.

Stage 2

The preparation of 1,3-bis-(2,4-diaminophenoxy)-propane-tetrahydrochloride was similar to Stage 2 of Example 1.

EXAMPLE 4

Stage 1

The preparation of 1,3-bis-(2,4-dinitrophenoxy)-propane was similar to that of Stage 1 of Example 1, only that diethylene glycol monomethyl-ether was used as a solvent. The yield of the desired intermediate product was 7.5 g, that is, 74% of theory.

Stage 2

The further processing to the end product was identical with the procedure in Stage 2 of Example 1.

EXAMPLE 5

Stage 1

The preparation of 1,3-bis-(2,4-dinitrophenoxy)-propane corresponded to Stage 1 of Example 1 with dimethyl formamide as a solvent. An amount of 5.1 g of the desired product was obtained, that is, 50% of theory.

Stage 2

The further processing to 1,3-bis-(2,4-diaminophenoxy)-propane-tetrahydrochloride corresponded to Stage 2 of Example 1.

Two of the bis-(2,4-diaminophenoxy)-alkanes described above, bis-(2,4-diaminophenoxy)-methane-tetrahydrochloride (A) and 1,2-bis-(2,4-diaminophenoxy)-ethane tetrahydrochloride (B), were used as coupler components in the following examples. The following substances were used as developer components:

E1: 2,4,5,6-tetraaminopyrimidine
E2: p-toluylene diamine
E3: p-phenylene diamine
E4: 2,5-diaminoanisol
E5: N,N,bis-($\beta$-hydroxyethyl)-p-phenylene diamine
E6: 2-anilino-2-hydroxy-5,6-diaminopyrimidine
E7: N,N-diethyl-2-methyl-p-phenylene diamine
E8: 2-chloro-p-phenylene diamine
E9: N-butyl-N-sulfobutyl-p-phenylene diamine
E10: 1-phenyl-3-carbamoyl-4-amino-pyrazolone.

The hair dyes according to the invention were used in the form of a cream emulsion by incorporating 0.01 mol of one of the developer and coupler substances listed in the Table below in an emulsion comprising:

(i) 10 parts by weight fatty alcohols of the chain length $C_{12}$–$C_{18}$,
(ii) 10 parts by weight fatty alcohol sulfate (sodium salt) of the chain length $C_{12}$–$C_{18}$, and
(iii) 75 parts by weight water.

Then, the pH-value of the emulsion was adjusted to a value of 9.5 by means of ammonia, and the emulsion was filled up with water to 100 parts by weight. The oxidative coupling was effected either with atmospheric oxygen or with a 1% solution of hydrogen peroxide as an oxidant by adding 10 parts by weight hydrogen peroxide solution to 100 parts by weight of the emulsion. The respective creams were applied with or without oxidants, on 90% grey human hair without special treatment and left there for 30 minutes. After the dyeing process was complete, the hair was washed with a conventional shampoo and subsequently dried. The resulting colors are compiled in the table below:

TABLE 1

| | | | COLORS OBTAINED | |
| --- | --- | --- | --- | --- |
| Example | Developer | Coupler | Oxidation with Atmospheric Oxygen | Oxidation with 1% $H_2O_2$ Solution |
| 6 | E1 | A | turquoise | dark turquoise |
| 7 | E2 | A | blue-black | blue-black |
| 8 | E3 | A | blue-black | blue-black |
| 9 | E1 | B | grey-turquoise | mat blue |
| 10 | E2 | B | mat blue | black blue |
| 11 | E4 | B | dark blue | dark blue |
| 12 | E5 | B | grey-turquoise | dark blue |
| 13 | E6 | B | mat violet | dark violet |
| 14 | E7 | B | dark turquoise | dark blue |
| 15 | E8 | B | violet-grey | dark violet |
| 16 | E9 | B | mat green | grey-turquoise |
| 17 | E10 | B | grey-violet | dark violet |

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. An aqueous preparation of the developer-coupler type for the dyeing of hair, consisting essentially of (A), as coupler, a bis-(2,4-diaminophenoxy)-alkane of formula

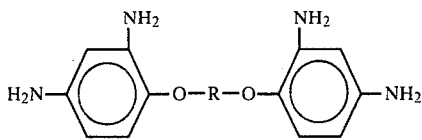

wherein R is a linear or branched alkylene radical of from 1 to 12 carbon atoms, or an inorganic or organic acid salt thereof, and (B), as developer, one of the conventional developer substances.

2. The aqueous preparation of claim 1 which contains from about 0.2 to 5% by weight of the developer-coupler combination, based on the total weight of the preparation.

3. The aqueous preparation of claim 2 which contains from about 1 to 3% by weight of the developer-coupler combination, based on the total weight of the preparation.

4. A process for the dyeing of hair which comprises applying to said hair for a time sufficient to effect dyeing through oxidation, an effective amount of the aqueous preparation of claim 1.

5. The process of claim 4 wherein the aqueous preparation is applied at temperatures ranging from about 15° to 40° C.

6. The process of claim 4 wherein the oxidation is also effected by the action of a chemical oxidizing agent.

* * * * *

UNITED STATES PATENT AND TRADEMARK OFFICE
CERTIFICATE OF CORRECTION

PATENT NO. : 4,314,809
DATED : February 9, 1982
INVENTOR(S) : DAVID ROSE et al.

It is certified that error appears in the above—identified patent and that said Letters Patent is hereby corrected as shown below:

Column 1, line 33, "nitrolphenol" should read -- nitrophenol --.

Column 2, line 52, "abovedescribed" should read -- above-described --.

Column 5, line 19, "by dye" should read -- the dye --.

Column 6, line 64, "dimethyl-" should read -- diethyl- --.

Signed and Sealed this

Twenty-fifth Day of May 1982

[SEAL]

Attest:

*Attesting Officer*

GERALD J. MOSSINGHOFF
*Commissioner of Patents and Trademarks*